(12) United States Patent
Tsai

(10) Patent No.: US 8,889,415 B2
(45) Date of Patent: Nov. 18, 2014

(54) METHOD FOR EXPANSION OF HUMAN CORNEAL ENDOTHELIAL CELLS

(76) Inventor: Ray Jui-Fang Tsai, Taipei (TW)

( * ) Notice: Subject to any disclaimer, the term of this patent is extended or adjusted under 35 U.S.C. 154(b) by 1843 days.

(21) Appl. No.: 11/741,903

(22) Filed: Apr. 30, 2007

(65) Prior Publication Data

US 2007/0254361 A1    Nov. 1, 2007

Related U.S. Application Data

(60) Provisional application No. 60/745,952, filed on Apr. 28, 2006.

(51) Int. Cl.
*C12N 5/074* (2010.01)
*C12N 5/0789* (2010.01)
*C12N 5/079* (2010.01)
*C12N 5/0797* (2010.01)
*C12N 5/071* (2010.01)
*C12N 5/00* (2006.01)
*A61L 27/38* (2006.01)
*A61L 27/36* (2006.01)
*A61K 35/12* (2006.01)

(52) U.S. Cl.
CPC ............ *C12N 5/0623* (2013.01); *C12N 5/0621* (2013.01); *A61L 27/3895* (2013.01); *C12N 2502/02* (2013.01); *C12N 2500/38* (2013.01); *C12N 2501/11* (2013.01); *A61L 27/3808* (2013.01); *A61L 27/3839* (2013.01); *A61L 27/3604* (2013.01); *C12N 2533/92* (2013.01); *A61L 2430/16* (2013.01); *A61K 35/12* (2013.01); *C12N 2501/115* (2013.01); *Y10S 977/913* (2013.01); *Y10S 977/904* (2013.01); *Y10S 977/923* (2013.01); *Y10S 977/908* (2013.01)
USPC ........... 435/395; 435/396; 435/397; 435/398; 435/402; 435/401; 435/366; 435/325; 435/368; 977/913; 977/904; 977/923; 977/908

(58) Field of Classification Search
None
See application file for complete search history.

(56) References Cited

U.S. PATENT DOCUMENTS

| | | | |
|---|---|---|---|
| 6,679,898 B1 * | 1/2004 | Chuck | 606/166 |
| 2005/0013806 A1 * | 1/2005 | Chang et al. | 424/93.21 |
| 2005/0214259 A1 * | 9/2005 | Sano et al. | 424/93.7 |

OTHER PUBLICATIONS

Terry, Eye, 2003, 17: 982-988.*
Supplemental European Search Report for the corresponding European Patent Application No. 07761578.9; dated Jun. 3, 2009; 8 pages.
Yutaka Ishino et al.; "Amniotic membrane as a carrier for cultivated human corneal endothelial cell transplantation"; Investigative Ophthalmology & Visual Science; Mar. 2004, vol. 45, No. 3; pp. 800-806.
Pan Z. et al.; "Transplantation of corneal stem cells cultured on amniotic membrane for corneal burn: experimental and clinical study"; Chinese Medical Journal; May 2002; vol. 115, No. 5; pp. 767-769.
Song E et al.; "Transplantation of human limbal cells cultivated on amniotic membrane for reconstruction of rat corneal epithelium after alkaline burn"; Chinese Medical Journal (English Edition); vol. 118, No. 11, 2005; pp. 927-935.

* cited by examiner

*Primary Examiner* — Chang-Yu Wang
(74) *Attorney, Agent, or Firm* — Wolf, Greenfield & Sacks, P.C.

(57) ABSTRACT

A method for expanding human corneal endothelial cells includes: (a) providing an amniotic membrane with or without amniotic cells, wherein the amniotic membrane has an extracellular matrix; (b) placing onto the amniotic membrane, a sheet of endothelial layer, or a cell suspension including human corneal endothelial stem cells; and (c) culturing the corneal endothelial cells on the amniotic membrane for a duration sufficient for the corneal endothelial stem cells to expand to an appropriate area. The invention also relates to a method for creating a surgical graft for a recipient site of a patient using the method for expanding human corneal endothelial cells, and the surgical graft prepared therefrom.

9 Claims, 1 Drawing Sheet

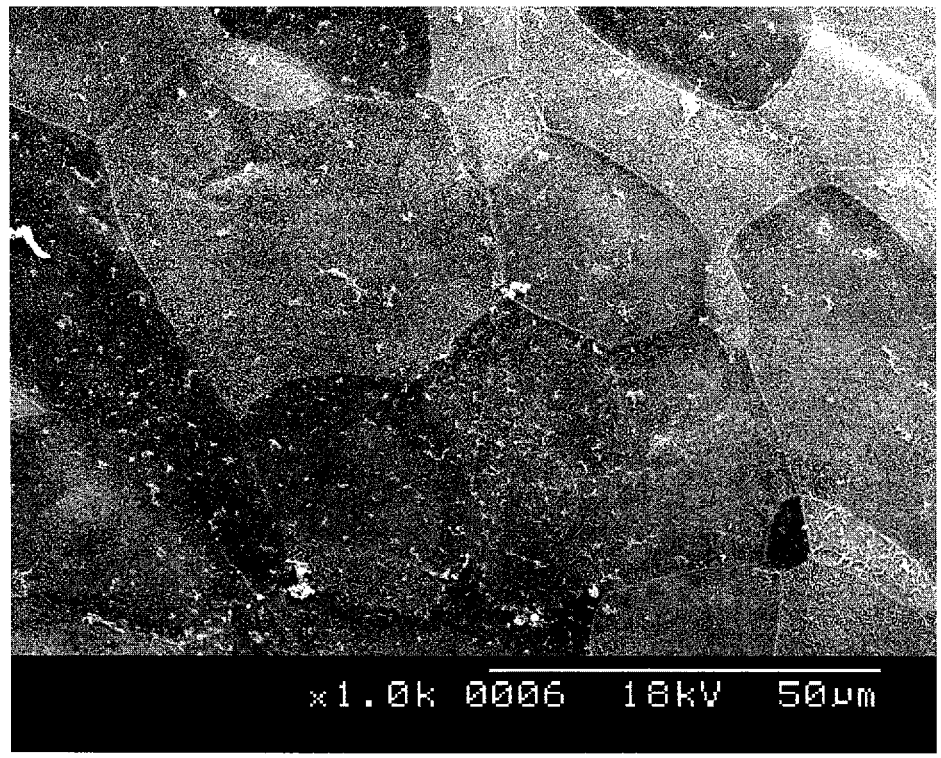

METHOD FOR EXPANSION OF HUMAN CORNEAL ENDOTHELIAL CELLS

CROSS-REFERENCE TO RELATED APPLICATIONS

This application claims priority from U.S. Provisional Application No. 60/745,952, filed Apr. 28, 2006, the entire disclosure of which is hereby incorporated herein by reference.

BACKGROUND OF THE INVENTION

This invention relates, in general, to a method for expanding corneal endothelial cells. More specifically, the invention relates to a method and a graft for treating problematic corneal endothelial cell decompensation in, for example, the reconstruction of corneal endothelium.

Corneal endothelial cells are a single layer of flat hexagonal cells that lie on a basement membrane, Descemet's membrane of the cornea, to form a pure cell sheet without any other cell types. The corneal endothelial cell is essential for maintaining corneal transparency. This function is dependent on endothelial regulation of stromal hydration, including the barrier and pump functions of the aqueous humor. Damage to the human corneal endothelial cells caused by intraocular surgery, glaucoma, trauma, or congenital corneal disease can result in irreversible corneal edema, at least in part because there is no or extremely low mitotic activity in the human corneal endothelial cell after birth, which leads to a gradual decrease in the cell population with age.

As corneal edema caused by damage of human corneal endothelial cells occurs, allograft posterior lamellar keratoplasty or penetrating keratoplasty is usually suggested as a remedy. One major concern of posterior lamellar keratoplasty or penetrating keratoplasty is that one donor cornea can only provide corneal endothelial layer replacement to one patient. Allograft rejection is another concern for penertrating keratoplasty. In addition, in many countries, the supply of donor corneas is insufficient.

Recently, it has been reported that the denuded amniotic membrane was used as a carrier for cultivated human corneal endothelial cell transplantation on the rabbit mode (Ishino Y. et al., *Invest Ophthalmol Vis Sci.* 2004; 45:800-806). However, according to the results, the amniotic membrane is not used for a substrate for ex vivo cell expansion.

BRIEF SUMMARY OF THE INVENTION

One aspect of the invention relates to a method for expanding human corneal endothelial cells, the method comprising:

(a) providing an amniotic membrane with or without amniotic cells, wherein the amniotic membrane has an extracellular matrix;

(b) placing onto the amniotic membrane, a sheet of endothelial layer, or a cell suspension including human corneal endothelial stem cells; and (c) culturing the corneal endothelial cells on the amniotic membrane for a duration sufficient for the corneal endothelial stem cells to expand to an appropriate area.

One other aspect of the invention relates to a method for creating a surgical graft for a recipient site of a patient, the method comprising:

(a) providing an amniotic membrane with or without amniotic cells, wherein the amniotic membrane has an extracellular matrix;

(b) placing onto the amniotic membrane, a sheet of endothelial layer, or a cell suspension including human corneal endothelial stem cells; and (c) culturing the corneal endothelial cells on the amniotic membrane for a duration sufficient for the corneal endothelial stem cells to expand to an appropriate area;

(d) separating the cultured corneal endothelial cells from the amniotic membrane; and (e) transplanting the cells obtained in step (d) onto a carrier to obtain a surgical graft.

Another aspect of the invention relates to a surgical graft, which is prepared by the above-mentioned method of the invention.

A further aspect of the invention relates to a method for treating an injured site deficient in corneal endothelial cells in a patient, the method comprising:

(a) providing an amniotic membrane with or without amniotic cells, wherein the amniotic membrane has an extracellular matrix;

(b) placing onto the amniotic membrane, a sheet of endothelial layer, or a cell suspension including human corneal endothelial stem cells; and (c) culturing the corneal endothelial cells on the amniotic membrane for a duration sufficient for the corneal endothelial stem cells to expand to an appropriate area;

(d) separating the cultured corneal endothelial cells from the amniotic membrane; and (e) transplanting the cells obtained in step (d) onto a carrier to obtain a surgical graft; and (f) attaching the surgical graft obtained in step (e) to the injured site.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a scanning electron microscopic (SEM) image showing human corneal endothelial stem cells expanded ex vivo, and then transplanted on a human corneal disc in accordance with one embodiment of the present invention.

DETAILED DESCRIPTION OF THE INVENTION

In one embodiment, the present invention relates to a method for expanding human corneal endothelial cells, the method comprising:

(a) providing an amniotic membrane with or without amniotic cells, wherein the amniotic membrane has an extracellular matrix;

(b) placing onto the amniotic membrane, a sheet of endothelial layer, or a cell suspension including human corneal endothelial stem cells; and (c) culturing the corneal endothelial cells on the amniotic membrane for a duration sufficient for the corneal endothelial stem cells to expand to an appropriate area.

According to the invention, an amniotic membrane is used for expanding human corneal endothelial cells. The amniotic membrane may be with or without amniotic cells, wherein the amniotic membrane has an extracellular matrix. According to one embodiment of the present invention, the corneal endothelial stem cells are expanded by culturing ex vivo on a basement membrane side of the amniotic membrane. The corneal endothelial stem cells are mounted on the basement membrane side of the amniotic membrane such that the corneal endothelial cells are positioned face up with reference to the basement membrane. The corneal endothelial stem cells are cultured on the amniotic membrane for a duration sufficient for the corneal endothelial stem cells to expand to an appropriate area or size, such as an area of about 2 cm to about 3 cm in diameter.

The amniotic membrane provides a special niche substrate to facilitate expansion of the corneal endothelial stem cell populations. In an example of the invention, after the corneal endothelial cells are expanded on the amniotic membrane, the corneal endothelial cells are separated from the amniotic membrane and transplanted onto a carrier to obtain a surgical graft. Then, the cultured or cultivated corneal endothelial cells on the denuded posterior corneal surface are then transplanted to a patient's eye.

According to another embodiment, the present invention also relates to a method for creating a surgical graft for a recipient site of a patient, comprising:

(a) providing an amniotic membrane with or without amniotic cells, wherein the amniotic membrane has an extracellular matrix;

(b) placing onto the amniotic membrane, a sheet of endothelial layer, or a cell suspension including human corneal endothelial stem cells; and (c) culturing the corneal endothelial cells on the amniotic membrane for a duration sufficient for the corneal endothelial stem cells to expand to an appropriate area;

(d) separating the cultured corneal endothelial cells from the amniotic membrane; and (e) transplanting the cells obtained in step (d) onto a carrier to obtain a surgical graft.

According to embodiments of the invention, the carrier used in step (d) of the method discussed immediately above may be a corneal disc, a thin layer of a treated or modified amniotic membrane, or any appropriate substrate that can carry the cells. In one embodiment of the invention, the carrier may be a disc of a size of about 8.5 mm to about 9.0 mm. The disc is less than about 100 μm in thickness. The corneal disc may be a thin denuded posterior corneal layer, taken from the patient or a donor from the eye bank. In an example of the invention, the corneal disc is a posterior corneal layer containing Descemet's membrane.

In embodiments of the invention, the corneal endothelial stem cells are human corneal endothelial cells obtained from an endothelial layer of a posterior limbal biopsy performed on a healthy eye of the patient, or an endothelial layer taken from a donor, preferably a peripheral corneal endothelial layer.

The present invention also relates to a surgical graft for an injured site deficient in corneal endothelial cells in a patient, which is prepared by the method as described above.

The invention further relates to a method for treating an injured site deficient in corneal endothelial cells in a patient, wherein the method comprises:

(a) providing an amniotic membrane with or without amniotic cells, wherein the amniotic membrane has an extracellular matrix;

(b) placing onto the amniotic membrane, a sheet of endothelial layer, or a cell suspension including human corneal endothelial stem cells; and (c) culturing the corneal endothelial cells on the amniotic membrane for a duration sufficient for the corneal endothelial stem cells to expand to an appropriate area;

(d) separating the cultured corneal endothelial cells from the amniotic membrane; and (e) transplanting the cells obtained in step (d) onto a carrier to obtain a surgical graft; and (f) attaching the surgical graft obtained in step (e) to the injured site.

The invention will now be described in further detail with reference to the following specific, non-limiting examples.

Example 1

Preparation of Human Corneal Endothelial Stem Cells from Limbal Biopsy for Culture A sector of peripheral endothelial layer was obtained by biopsy from the same eye or the other eye of the patient being treated or from another living individual during a trabeculectomy procedure. The eye lid was sterilized with povidone-iodine. Under sterile conditions, a conjunctival flap was created for about 8 mm in length with a limbal base about 5 mm to about 6 mm from the limbus. A limbal base of a scleral flap having a dimension of about 5 mm in length and about 400 μm in depth was created about 3 mm from the limbus, and the flap was extended to the cornea and about 2 mm from the limbus. An anterior chamber was entering from the limbal area and extending for about 3 mm in length parallel around the limbal zone when the sclerocorneal flap was lifted. Trabeculectomy was performed and corneal endothelial layer was separated from the removed tissue. The removed corneal endothelium was then used for culture. The sclerocorneal flap and conjunctival wound were closed with 10-0 nylon suture.

Example 2

Preparation of Human Corneal Endothelial Stem Cells from Donor Cornea

A sector of peripheral corneal endothelial layer was also obtained from a donor cornea. A sclerocorneal rim of the donor cornea was obtained when the central cornea was trephined for penetrating keratoplasty. The corneal endothelial layer with Descemet's membrane was separated carefully from the trabecular meshwork with surgical blade No. 15. Six sectors of peripheral corneal endothelial layer were obtained from one donor cornea.

The sector of peripheral corneal endothelial layer containing corneal endothelial stem cells was placed in a 35 mm dish containing 1.5 ml of culture medium. The culture medium was OPTIMEM-1 (purchased from Invitrogen, San Diego, Calif., USA) as a basal medium, supplemented with 5% to 8% patient's serum, and 10 ng/ml of Fibroblast Growth Factor (FGF), 5 ng/ml Epidermal Growth Factor (EGF), 10 μg/ml of ascorbic acid, 50 μg/ml penicillin, 50 μg/ml streptomycin, 2.5 mg/ml fungizone. The sector in the dish was sent immediately to the laboratory for culture in a sterile, laminar flow hood.

Example 3

Preparation of Human Amniotic Membrane and Expansion of Human Corneal Endothelial Stems Cells on the Human Amniotic Membrane In accordance with the tenets of the Declaration of Helsinki and with proper informed consent, a human amniotic membrane was obtained at the time of cesarean section. The human amniotic membrane was washed with PBS containing antibiotics (5 ml of 0.3% ofloxacin) and then stored in DMEM and glycerol at −80° C.

The amniotic membrane, with basement membrane side up, was affixed smoothly onto a culture plate and placed at 37° C. under 5% $CO_2$ and 95% air, in a humidified incubator overnight before use. The corneal endothelial explant culture was performed on the amniotic membrane. The peripheral corneal endothelial layer containing corneal endothelial stem cells was planted or transferred onto the basement membrane side of the amniotic membrane in a 35 mm dish containing about 1 ml to about 1.5 ml of the culture medium described above. The medium was changed every two days, and the culture was maintained for 2 to 4 weeks, by which time the corneal endothelial stem cells had grown and spread to an area of about 2 cm to about 3 cm in diameter. Cultured human corneal endothelial stem cells were detached from the culture dish by treating with 1.2 IU dispase II at 37° C. for about one hour to about two hours, then to a mixture of trypsin and ethylenediaminetetraacetic acid (EDTA) for another several hours to obtain cell suspensions for passage.

Example 4

Preparation of Human Corneal Disc and Transplantation of Expanded Human Corneal Endothelial Stems Cells onto the Human Corneal Disc The freshly prepared full thickness central corneal disc including diseased endothelial cells was obtained from the patient with bullous keratopathy during penertrating keratoplasty. The full thickness central corneal disc was placed in a 35 mm dish containing 1.5 ml of the culture medium as described in Example 2 above. The corneal disc in the dish was sent immediately to the laboratory for culture in a sterile, laminar flow hood. The diseased endothelial cells were denuded by 0.02 mg/ml trypsin/EDTA in Hank's Balanced Salt Solution (HBSS) incubated for 1 hour at 37° C. The cells were detached with vigorous disruption using a flame-polished pipette. The denuded corneal disc with Descemet's membrane side up was placed on a 24-well dish. A small volume (0.3 ml to 0.5 ml) of the passage cell suspension as obtained in Example 3, containing approximately $2 \times 10^5$ cells was then pipetted onto the Descemet's membrane of the denuded corneal disc cultured with the culture medium as described in Example 2 above and cultured for about 10 to about 14 days. After cell transplantation, the cornea was incubated in medium F99 (Ham's F12/Medium 199) with descending serum concentrations (10%, 5%, 2%) at 37° C. for about one week. The transplantation success was morphologically evaluated using microscopy and scanning electron microscopy.

Referring to FIG. 1, a scanning electron microscopic image at 1000× magnification, showed that the ex vivo expanded human corneal endothelial stem cells were transplanted on the human corneal disc according to one embodiment of the present invention. A peripheral zone of human corneal endothelial cells contain high proliferative capacity for proliferation and passages. Auto-graft or allo-graft of ex vivo expanded human corneal endothelial cells and endothelial keratoplasty provides an optimal solution to future corneal reconstruction.

The unique technique for ex vivo expansion of on pretreated amniotic membrane substrate ensures passage and transplantation of healthy and young human corneal endothelial stem cells to recipient cornea. When the transplantation is conducted using autologous corneal endothelial stem cells, the expanded human corneal endothelial stem cells will provide the beneficial effect that requires no immunosuppression after transplantation. For allogeneic corneal endothelial stem cells transplanted in this manner, the rejection rate is also lessened, since only corneal endothelial stem cells exclusive of other cell types are transplanted.

It is believed that a unique and inventive surgical graft and method of its creation have been disclosed sufficiently for those skilled in the art to practice the invention without significant experimentation, as well as develop modifications which lie within the spirit and scope of the invention as defined by its claims.

I claim:

1. A method for creating a surgical graft, the method comprising: (a) culturing human corneal endothelial stem cells on a first substrate to allow expansion of the corneal endothelial stem cells, wherein the first substrate is an amniotic membrane having an extracellular matrix; (b) separating the expanded human corneal endothelial stem cells from the amniotic membrane; and (c) placing the cells obtained in (b) on a second substrate to obtain the surgical graft; wherein the second substrate is a corneal disc or a thin layer of an amniotic membrane.

2. The method of claim 1, wherein in (a), the corneal endothelial stem cells are cultured ex vivo on a basement membrane side of the amniotic membrane.

3. The method of claim 1, wherein in (a), the corneal endothelial stem cells are obtained from a corneal endothelial layer of a posterior limbal biopsy performed on a healthy eye of the patient.

4. The method of claim 1, wherein in (a), the corneal endothelial stem cells are obtained from an endothelial layer taken from a donor.

5. The method of claim 4, wherein the endothelial layer is a peripheral corneal endothelial layer.

6. The method of claim 1, wherein the second substrate is less than about 100 um in thickness.

7. The method of claim 1, wherein the second substrate is a corneal disc.

8. The method of claim 7, wherein the corneal disc is a thin denuded posterior corneal layer.

9. The method of claim 7, wherein the corneal disc is a posterior corneal layer containing Descemet's membrane.

* * * * *